(12) United States Patent
Desilets et al.

(10) Patent No.: US 7,766,848 B2
(45) Date of Patent: *Aug. 3, 2010

(54) MEDICAL ULTRASOUND TRANSDUCER HAVING NON-IDEAL FOCAL REGION

(75) Inventors: Charles S. Desilets, Edmonds, WA (US); Jens U. Quistgaard, Seattle, WA (US)

(73) Assignee: Medicis Technologies Corporation, Bothell, WA (US)

( * ) Notice: Subject to any disclaimer, the term of this patent is extended or adjusted under 35 U.S.C. 154(b) by 161 days.

This patent is subject to a terminal disclaimer.

(21) Appl. No.: 11/439,706

(22) Filed: May 23, 2006

(65) Prior Publication Data

US 2007/0035201 A1    Feb. 15, 2007

Related U.S. Application Data

(63) Continuation-in-part of application No. 10/816,197, filed on Mar. 31, 2004, now Pat. No. 7,273,459.

(60) Provisional application No. 60/459,355, filed on Mar. 31, 2003, provisional application No. 60/483,317, filed on Jun. 26, 2003.

(51) Int. Cl.
*A61B 8/00* (2006.01)

(52) U.S. Cl. .................. 601/3; 600/459; 310/334; 310/371

(58) Field of Classification Search .......... 600/439, 600/459; 601/2–4; 73/514.34; 310/311, 310/334, 371
See application file for complete search history.

(56) References Cited

U.S. PATENT DOCUMENTS

| | | |
|---|---|---|
| 4,002,221 A | 1/1977 | Buchalter |
| 4,059,098 A | 11/1977 | Murdock |
| 4,211,949 A | 7/1980 | Brisken et al. |
| 4,291,578 A | 9/1981 | Hetz et al. |
| 4,326,418 A | 4/1982 | Pell, Jr. |
| 4,368,410 A | 1/1983 | Hance et al. |
| 4,437,033 A | 3/1984 | Diepers |
| 4,459,854 A | 7/1984 | Richardson et al. |

(Continued)

FOREIGN PATENT DOCUMENTS

EP    0 206 432 A    12/1986

(Continued)

OTHER PUBLICATIONS

Ayme et al., Occurance of transient cavitation in pulsed swatooth ultrasonic fields *J. Acoust. Soc. Am.* (1988) 84(5):1598-1605.

(Continued)

*Primary Examiner*—Brian Casler
*Assistant Examiner*—Jonathan G Cwern
(74) *Attorney, Agent, or Firm*—Townsend and Townsend and Crew LLP

(57) ABSTRACT

A mechanically formed transducer capable of producing a non-ideal focal region is described. The transducer has a plurality of piezoelectric elements suspended in an epoxy and heat molded into a desired shape. One or more shaped irregularities in the transducer provides for a mechanically induced non-ideal focal field without the need for electronic steering or lens focusing. Systems and methods of making the same are also described.

8 Claims, 5 Drawing Sheets

U.S. PATENT DOCUMENTS

| | | |
|---|---|---|
| 4,501,557 A | 2/1985 | Tamura et al. |
| 4,556,066 A | 12/1985 | Semrow |
| 4,567,895 A | 2/1986 | Putzke |
| 4,593,699 A | 6/1986 | Poncy et al. |
| 4,865,042 A * | 9/1989 | Umemura et al. ........... 600/439 |
| 4,960,107 A | 10/1990 | Aida et al. |
| 5,143,063 A | 9/1992 | Fellner |
| 5,164,920 A | 11/1992 | Bast et al. |
| 5,259,383 A | 11/1993 | Holstein et al. |
| 5,301,660 A | 4/1994 | Rattner |
| 5,352,301 A | 10/1994 | Panchanathan et al. |
| 5,382,286 A | 1/1995 | Fanning et al. |
| 5,400,788 A | 3/1995 | Dias et al. |
| 5,402,792 A | 4/1995 | Kimura |
| 5,410,210 A * | 4/1995 | Sato et al. .................... 310/363 |
| 5,419,327 A | 5/1995 | Rohwedder et al. |
| 5,434,208 A | 7/1995 | Batelaan et al. |
| 5,476,438 A | 12/1995 | Edrich et al. |
| 5,477,736 A | 12/1995 | Lorraine |
| 5,505,206 A | 4/1996 | Walloch |
| 5,526,815 A | 6/1996 | Granz et al. |
| 5,568,810 A | 10/1996 | Hamers et al. |
| 5,623,928 A | 4/1997 | Wright et al. |
| 5,626,554 A | 5/1997 | Ryaby et al. |
| 5,669,150 A | 9/1997 | Guertin et al. |
| 5,676,159 A | 10/1997 | Navis |
| 5,738,098 A | 4/1998 | Brock-Fisher et al. |
| 5,738,635 A | 4/1998 | Chapelon et al. |
| 5,755,753 A | 5/1998 | Knowlton |
| 5,769,790 A | 6/1998 | Watkins et al. |
| 5,820,623 A | 10/1998 | Ng |
| 5,871,446 A | 2/1999 | Wilk |
| 5,873,845 A | 2/1999 | Cline et al. |
| 5,938,608 A | 8/1999 | Bieger et al. |
| 5,938,922 A | 8/1999 | Fulk, Jr. et al. |
| 6,039,689 A | 3/2000 | Lizzi |
| 6,039,694 A | 3/2000 | Larson et al. |
| 6,071,239 A | 6/2000 | Cribbs et al. |
| 6,085,749 A | 7/2000 | Wardle et al. |
| 6,113,558 A | 9/2000 | Rosenschein et al. |
| 6,142,748 A | 11/2000 | Harris et al. |
| 6,152,137 A | 11/2000 | Schwartz et al. |
| 6,217,515 B1 | 4/2001 | Yamakawa et al. |
| 6,233,476 B1 | 5/2001 | Strommer et al. |
| 6,241,703 B1 | 6/2001 | Levin et al. |
| 6,261,249 B1 | 7/2001 | Talish et al. |
| 6,264,605 B1 | 7/2001 | Scirica et al. |
| 6,302,848 B1 | 10/2001 | Larson et al. |
| 6,306,146 B1 | 10/2001 | Dinkler |
| 6,312,386 B1 | 11/2001 | Bolorforosh et al. |
| 6,366,831 B1 | 4/2002 | Raab |
| 6,419,648 B1 | 7/2002 | Vitek et al. |
| 6,423,077 B2 | 7/2002 | Carol et al. |
| 6,488,639 B1 | 12/2002 | Ribault et al. |
| 6,506,171 B1 | 1/2003 | Vitek et al. |
| 6,554,826 B1 | 4/2003 | Deardorff |
| 6,561,389 B1 | 5/2003 | Earle |
| 6,575,906 B1 | 6/2003 | Schembri, Jr. et al. |
| 6,607,498 B2 | 8/2003 | Eshel |
| 6,613,004 B1 | 9/2003 | Vitek et al. |
| 6,618,620 B1 | 9/2003 | Freundlich et al. |
| 7,273,459 B2 * | 9/2007 | Desilets et al. ................ 601/2 |
| 2002/0128592 A1 | 9/2002 | Eshel |
| 2003/0083536 A1 | 5/2003 | Eshel et al. |
| 2004/0039312 A1 | 2/2004 | Hillstead et al. |

FOREIGN PATENT DOCUMENTS

| | | |
|---|---|---|
| EP | 0 367 117 A2 | 5/1990 |
| FR | 2 679 125 A1 | 1/1993 |
| GB | 820814 | 9/1959 |

OTHER PUBLICATIONS

Billard et al., Effects of Physical Parameters on High Temperature Ultrasound Hyperthermia, *Ultrasound in Med. & Biol.* (1990) 16(4):409-420.

Cain et al., Concentric-Ring and Sector-Vortex Phased-Array Applicators for Ultrasound Hyperthermia, *IEEE Transactions on Microwave Theory and Techniques*, (1986) MTT-34(5):542-551.

Chen et al., Mechanisms of Lesion Formation in High Intensity Focused Ultrasound Therapy, *2002 IEEE Ultrasonics Symposium*, (2002) pp. 1443-1446.

Clarke et al., Physical and chemical aspects of ultrasonic disruption of cells *J. Acoust. Soc. Am.* (1970) 47(2):649-653.

Fjield et al., Design and Experimental Verification of Thin Acoustic Lenses for the Coagulation of Large Tissue Volumes, *Phys. Med. Biol.* (1977) 42:2341-2354.

Fjield et al., Experimental verification of the sectored annular phased array for MRI guided ultrasound surgery *IEEE Ultrasonics Symposium* (1996) pp. 1273-1276.

Fjield et al., The Combined Concentric-Ring and Sector-Vortex Phased Array for MRI Guided Ultrasound Surgery, *IEEE Transactions on Ultrasonics, Ferroelectrics, and Frequency Control* (1997) 44(5):1157-1167.

Fjield et al., In Vivo Verification of the Acoustic Model Used to Predict Temperature Elevations for MRI Guided Ultrasound Surgery, *1998 IEEE Ultrasonics Symposium*, (1998) pp. 1415-1418.

Flynn et al., A mechanism for the generation of cavitation maxima by pulsed ultrasound *J. Acoust. Soc. Am.* (1984) 76(2):505-512.

Fry, Precision High Intensity Focusing Ultrasonic Machines for Surgery, *From the Biophysical Research Laboratory, College of Engineering, University of Illinois, Urbana, Illinois*, (1958) pp. 152-156.

Fry et al., Threshold ultrasonic dosages for structural changes in the mammalian brain *J. Acoust. Soc. Am.* (1970) 48(6):1413-1417.

Ter Haar, Ultrasound Focal Beam Surgery, *Ultrasound in Med. & Biol.*, (1995) 21(9):1089-1100.

Hand, Ultrasound Hyperthermia and the Prediction of Heating, *Ultrasound in Medicine*, Duck et al., Eds., Chapter 8, Institute of Physics Publishing, Bristol and Philadelphia, (1998) pp. 151-157.

Kinney, Body contouring with external ultrasound *Plastic & Reconstruct. Surg.* (1999) 103:728-729.

Padmaker, Thresholds and mechanisms of ultrasonic damage to 'organized' animal tissues *Symposium on Biological Effects and Characterizations of Ultrasound Sources* (1977) Hazzard et al., Eds., pp. 224-239.

Umemura, The Sector-Vortex Phased Array: Acoustic Field Synthesis for Hyperthermia, *IEEE Transactions on Ultrasonics, Ferroelectrics, and Frequency Control*, (1989) 36(2):249-257.

* cited by examiner

MEDICAL ULTRASOUND TRANSDUCER HAVING NON-IDEAL FOCAL REGION

CROSS-REFERENCES TO RELATED APPLICATIONS

The present application is a continuation-in-part from U.S. patent application Ser. No. 10/816,197 entitled "Vortex Transducer," filed on Mar. 31, 2004, now U.S. Pat. No. 7,273,459, which claimed the benefit of Provisional Application No. 60/459,355, filed Mar. 31, 2003, and of Provisional Application No. 60/483,317, filed on Jun. 26, 2003, the full disclosures of which are incorporated herein by reference.

BACKGROUND OF THE INVENTION

1. Field of the Invention

The present invention relates to an ultrasound transducer for the use in high intensity focused ultrasound (HIFU) applications for medical applications.

2. Description of the Background Art

Lysis (the process of disintegration or dissolution) of human tissue using high intensity focused ultrasound (HIFU) is a technique that has been studied for over 50 years. Research into applications of HIFU have revolved mostly around treating malignant tumors in the body either untreatable by other means, or promising a more efficacious treatment modality. HIFU commercialization has been very slow to develop, however, despite some of its early promise. Reasons for this include the inability to visualize the lesions being formed, the necessity of having to lyse an entire malignant tumor to be considered effective, and especially the extended period of time required to lyse a significant volume of tissue. In the last 10 years or so, some companies have been formed to commercialize HIFU for non-cancerous treatment applications. The best-known example is the treatment of enlarged prostate or BPH. Here, it is not necessary to lyse all the tissue to be effective. Advances in the treatment of BPH with drugs, however, has seriously shrunk the commercial prospects for this case. Advances in MRI and diagnostic ultrasound in the last 20 years have aided visualization of HIFU lesions, alleviating a main obstacle to the commercial advancement of the field. Additionally, where small volumes of tissue can be treated, as in hemostasis and blood clot breakup, HIFU is likely to prove to be viable commercially. Lysing large volumes of tissue, as in the case of removing significant amounts of adipose tissue, requires additional technical strategies.

Cross-sectional histological views of a HIFU lesion formed in vivo in porcine adipose tissue are shown at 40× (FIG. 1) and at 200× (FIG. 2). Tri-chrome staining is employed. Lysed tissue shows blood perfusion around individual fat cells and incursion of phagocytes and red blood cells into the HIFU-treated volume. Lesions formed with HIFU are typically cigar-shaped, with lesions lengths being 5-8 times the lesion diameters. HIFU lesions are typically formed by spherically focusing an ultrasonic beam. These lesions can be as little as 1-2 mm in diameter, and 6-10 mm in length. It would take many lesions to necrose a large volume of tissue. Preferred thermal processes of gradual heating are generally slow, so that it may take up to 30 seconds to generate enough absorption of the ultrasonic energy to raise the temperature high enough to necrose tissue, and additional time to allow the temperature of tissue between the skin and treated volume to cool sufficiently before the next lesion is created. A simple calculation shows that it could take hours to ablate a volume of tissue on the order of 250 cc with a single transducer making individual lesions. Diminishing the time required to ablate a large volume of tissue, as in adipose tissue reduction, could mean the difference between a successful commercial product and an unsuccessful one.

Several strategies can be employed to reduce the time between making individual lesions include using multiple mechanically scanned HIFU transducers, scanning the transducer(s) continuously, and/or using some kind of linear or 2D transducer array or structure to generate multiple focal spots. While some combination of these strategies could be employed, a major physical limitation of reducing scanning time remains the small diameter of the focused ultrasound beam. A defocusing strategy holds some promise of increasing the effective spot size by spreading the energy more laterally than lengthwise, creating a more spherical-shaped lesion. "Wobbling" the HIFU transducer mechanically about its axis could serve to do this, and such ideas have been reported in the literature. However, it would be certainly less complicated and expensive to build the defocusing into the HIFU transducer itself.

A method of creating an annular focal zone where the diameter of the annulus is adjustable has been reported by Cain and Umemura (Cain, Charles A. and Shin-Ichiro Umemura, "Concentric-Ring and Sector-Vortex Phased-Array Applicators for Ultrasound Hyperthermia", *IEEE Trans. on Microwave Theory and Techniques*, Vol MTT-34, No. 5, May 1986, pp. 542-551.) and (Umemura, Shin-Ichiro and C. A. Cain, "The Sector-Vortex Phased Array: Acoustic Field Synthesis for Hyperthermia", *IEEE Trans. on Ultrasonics, Ferroelectrics, and Frequency Control*, Vo. 36, No. 2, March 1989, pp. 249-257.) and Hynynen et. al. (Fjield, T., V. Sorrentino, H. Cline, and K. Hynynen, "Design and experimental verification of thin acoustic lenses for the coagulation of large tissue volumes", *Phys. Med. Biol.*, Vol 42, 1997, pp. 2341-2354.) and (Fjield, T. and K. Hynynen, "Experimental Verification of the Sectored Annular Phased Array for MRI Guided Ultrasound Surgery", Proc 1996 IEEE Ultrasonics Symposium, pp. 1273-1276.) and (Fjield, T. and K. Hynynen, "The Combined Concentric-Ring and Sector-Vortex Array for MRI Guided Ultrasound Surgery", *IEEE Trans. on Ultrasonics, Ferroelectrics, and Frequency Control*, Vo. 44, No. 5, September 1997, pp. 1157-1167.) and (Fjield, T., N. McDannold, C. Silcox, and K. Hynynen, "In Vivo Verification of the Acoustic Model Used to Predict Temperature Elevations for MRI Guided Ultrasound Surgery", Proc 1998 IEEE Ultrasonics Symposium, pp. 1415-1418.). This concept, dubbed the sector-vortex array, has been implemented using electronic array techniques or simply adding a mechanical sector-vortex lens onto the front of a planar transducer. The effect of this lens is to create a double-cone field pattern that yields an annular ring in cross-section.

Extensive research with mechanically scanned, spherically focused transducers has been conducted in HIFU fat-tissue mimicking gel phantoms and in vivo porcine adipose tissue. The purpose of this research is to determine basic design parameters for optimizing the lysing of subcutaneous adipose tissue and develop candidate lysing and scanning protocols for inclusion into a product development specification and initial human safety trials. This research has shown that challenges remain in reducing the overall treatment time to the desired values. While various scanning strategies have proven fruitful in reducing the heat build-up tissue in the zone between the skin and HIFU-created focal volume, and thus reducing scanning time, even greater efficacy can be shown if the focal zone overall diameter is increased significantly. Transducers with built-in non-ideal focal region capability could prove to be a relatively simple, cost-effective means to achieve this capability.

Spherical focusing is typically achieved by bonding a plano-concave lens on to the front of a planar piezoelectric material, or shaping the piezoelectric material into a spherical bowl. High ultrasonic intensities (1-4 kW/cm$^2$) are created driving the piezoelectric material at very high power levels, and focusing the beam very tightly. Absorption of this energy by tissue elevates its temperature. Raising this temperature in excess of 60° C. in the focal zone coagulates cell proteins, thereby ablating the tissue. There is a very sharp line between ablated and unablated tissue, as seen in FIG. 1. If the intensity is high enough, the temperature rise is sufficient to cause boiling and the production of small bubbles, producing a lesion with the elongated shape of a weather balloon at high altitudes ("tadpole" shape to others). At an even higher threshold, inertial cavitation (bubble creation) may occur, which can lyse tissue through thermo-mechanical means.

Lesions made in vivo in porcine tissue with spherically focused transducers show remarkably similar characteristics to those made in adipose tissue. Cigar-shaped lesions are made at relatively low power levels at longer insonification times, following the 6 dB contour of a classically spherically focused lens, and elongated weather balloon-shaped lesions are made at relatively high power levels where suspected boiling creates bubbles which reflect acoustic power back to the skin surface. At very high power levels, or too long insonification times, excessive heat can be generated above the focal zone which will lyse tissue up to and including the skin surface. While large volumes of tissue can be lysed in this manner, controlling this type of lesion growth can be problematic when considering patient and environmental variability.

Reducing the focal intensity at the center of the lesion and spreading the energy out over a larger volume should help alleviate the creation of a boiling hot spot while allowing more energy to be deposited during an insonification period, ultimately reducing the scanning time.

Composite piezoelectric materials have been a subject of research and development for nearly 25 years. Ultrasonic transducers and arrays for diagnostic imaging purposes have been manufactured since the late 1980's, and have application in such diverse areas as sonar and non-destructive testing. One manufacturer (Imasonic, Besancon, FR) builds custom composite HIFU applicators which are used by several research and commercial organizations. Popularly known as piezocomposites, these materials are made by taking solid blocks of piezoelectric ceramic, dicing the block into a forest of tall, thin pillars of ceramic, and backfilling the dicing kerfs with a polymer. This composite ceramic/polymer material is then processed like a normal solid transducer ceramic into thin plates. The volume fraction of the composite is controlled by the dicing kerf width and spacing, and the composite material properties can thereby be tailored to specific applications.

While many superior properties of composites are exploited in diagnostic imaging, the chief interest for HIFU is the ability to form composites into arbitrary shapes. In diagnostic imaging, the superior piezoelectric and acoustic properties of composites are exploited to produce wideband frequency responses, which are of little interest in HIFU at this time. Flexible polymer materials are often used as composite fillers which allow the material to be easily manipulated into cylindrical or spherical shapes. However, flexible composites are inherently high loss materials and unsuitable to the high power levels used in HIFU. Flexible materials would distort and ultimately disintegrate due to the heat build-up inside the material itself under high drive levels. Using less flexible polymers as composite filler materials would increase the composites' power handling capabilities due to lower intrinsic loss mechanisms, but would then make forming the composite into a curved shape seemingly impossible.

The answer to this dilemma is to make use of an interesting property of many hardset epoxies: these materials can be heated at a relatively low temperature into a partially cured state (namely, a B-stage cure) that is quite hard, but fairly brittle. In this state, the material can be processed, that is diced, filled, ground, lapped, and electroded into the thin sheets needed for HIFU applicators, and then reheated to a temperature somewhat above the original B-stage cure temperature. At this point, the polymer softens considerably and can be clamped into a mold shaped to the configuration desired (for instance, a spherically shaped bowl or a shape to provide a non-ideal focal region) and reheated to a much higher temperature. The epoxy filler then will fully cure, and further heat treatment can elevate the epoxy glass transition temperature, the temperature at which the polymer suddenly will soften, to levels between 120° and 200° C. The material thus formed is relatively low loss and capable of handling HIFU power levels, albeit with less efficiency than solid, high power, piezoelectric ceramics.

While requiring custom molds and clamping equipment, ultimately it is easier and cheaper to produce ceramic elements this way than to grind them directly using expensive equipment or hand labor; the elements are more rugged as well, which is a very important consideration. The lower efficiency is not expected to be a limitation in fat lysis since higher frequencies can be used for the small treatment depths, and thus high intensities can be achieved with relatively low drive levels. This is easily demonstrated by considering the fact that the intensity antenna gain for a focused radiator increases as the square of the frequency. An optimum frequency for HIFU at a given depth of focus can be obtained from the following equation:

$$f_{opt}=1/(2\alpha z),$$

where $f_{opt}$ is the optimum frequency, $\alpha$ is the ultrasonic absorption of fat, and z is the tissue depth to be treated. For fat treated at 2 cm of depth, the optimum frequency for maximum heat deposition is 4.2 MHz. Other considerations may change the actual operating frequency, of course.

Clearly the marriage of a technique of increasing the focal area of a HIFU applicator like the vortex or non-ideal focal region concept and a means of easily and cheaply implementing this interesting structure like piezocomposites can reduce the overall treatment time for lysing large volumes of adipose tissue. Reducing treatment time and cost are key areas which will determine the fate of lysis commercialization efforts.

Sector-vortex array design has been extensively described and simulated by Cain and Umemura, Umemura and Cain, and numerous papers from Hynynen and co-workers at Brigham's and Women's Hospital at Harvard. They describe an implementation whereby the driving electrode of a spherical radiator is divided into N number of equal sized, pie-shaped sectors. Following Cain, driving signals are applied to the N sectors with a phase distribution over the N sectors determined by:

$$\phi=m(\theta_l),$$

for $l=1,2,\ldots N$ where m is the vortex mode number, and $\theta_l=i2\pi/N$. The phase distribution over the N sectors is such that that the excitation field rotates around the radiator at a phase velocity $\omega_0/m$. When N is large, an approximate analytic expression for the acoustic field in the focal plane can be derived; this field has a shape determined by the mth order Bessel function. The vortex-shaped field is zero along the central axis for ≠0, and has a diameter proportional to the vortex mode m. The field in cross-section resembles an annulus with side lobes at radii greater than the annulus.

However sector-vortex designs require complex electronics to drive the transducers in order to produce the vortex focal field. The electronics are required to drive either sector transducers or phased arrays in sequence. Some prior teachings rely on ancillary technologies such as the use of MRI machines to detect hotspots, and provide for additional electronic to provide real time corrections in the electronic firing of the various transducer elements to eliminate or reduce the occurrence of out-of-field ultrasound excitation. Complex lenses have also been described to facilitate the steering of the ultrasound energy into the body.

Thus there remains a need in the art for a robust vortex transducer, having a simplified design that can operate without the requirement of complex and expensive electronics.

There is further a need for a vortex transducer that can be aimed without the use of a lens.

There is still further a need for a vortex transducer having a fast activation and treatment time for reliably depositing a fixed amount of energy into a focal zone.

BRIEF SUMMARY OF THE INVENTION

At least some of the needs of the art are addressed by the present inventions. In accordance with the needs of the art, it is an objective of the present invention to provide a transducer capable of producing a vortex focal zone.

It is further an objective to provide a transducer able to create a vortex focal zone without the use of complex electronics.

It is still further an objective of the present invention to be able to reliably aim a vortex transducer without using a lens or electronic steering.

Yet another objective is to provide for a vortex transducer with a cheap and cost effective manufacturing process.

At least one of these objectives is met with a medical ultrasound transducer having an axis with a front and back surface transverse to the axis. The transducer has an edge or perimeter that is axially offset to produce at least one substantially annular 2 πm phase shift focal region(s) when the transducer is excited. The m variable is not a whole number. If the transducer has more than one offset, each offset may be the same or a different value.

In a second embodiment there is a medical ultrasound transducer having an axis with a front and back surface transverse to the axis. The transducer has two or more edges of the surface that are axially offset to produce a 2 πm phase shift focal region for each offset when said transducer is excited.

A method of manufacturing is disclosed comprising the steps of first shaping a piezoelectric ceramic into a desired form, the form having a front end and a back end. Second dicing the front end to create a plurality of elements, the elements being attached to the back end and separated by dicing channels. Third, filling the dicing channels with a polymer material and allowing the polymer to gel. Fourth, creating a transducer form by removing the back end such that the elements are separated from one another. Fifth, pressing the transducer form into a mold and heating the transducer form such that the resin is heated above the B-stage and allowing the resin to cross-link and cool in a set shape. Sixth, treating at least one surface of the transducer form with a conductive material such that all elements are in contact with the conductive material. An additional step involves the formation of a shaped irregularity to produce at least one substantially annular non-deal focal zone when the transducer is excited. This step can be inserted into the steps above where ever desired and there is no best order for the introduction of this step. The shaped irregularity can be part of the original forming of the transducer form, or it can be created later by cutting or grinding the transducer form such that the desired irregularity is introduced.

DETAILED DESCRIPTION OF THE INVENTION

Described herein is an implementation of a version of the sector-vortex concept. While this concept is known, this disclosure implements the design in a novel manner. In order to avoid the complexities and cost of an electronic beamformer, or the use of a sector-vortex lens with its attendant issues in reliability, acoustic losses and reverberations, and cooling, a continuous vortex lens can be incorporated into the piezoelectric transducer material itself. This can be done by building the transducer out of piezoelectric composite material which can be molded into a vortex lens. This eliminates the need for complex driving electronics and all the issues of an external lens. This design could be instrumental in building cheap, reliable devices that can potentially reduce treatment time by factors of two to eight.

Figure 1:
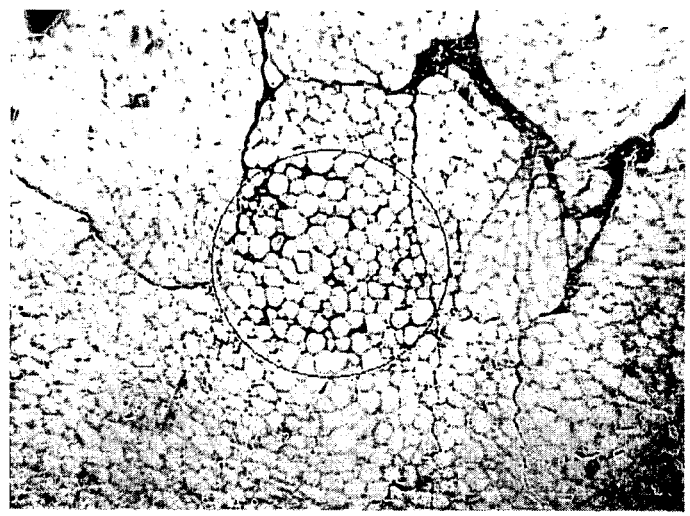
FIG. 1 is a histological view of a HIFU lesion in porcine adipose tissue at 40× magnification.
Figure 2:
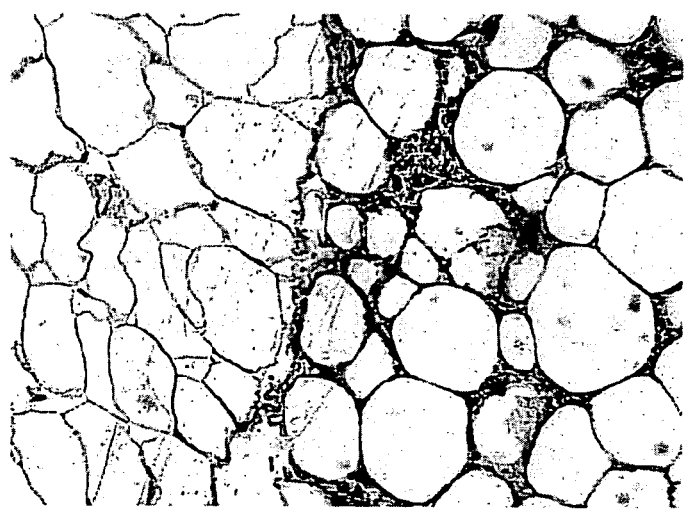
FIG. 2 is a histological view of a HIFU lesion in porcine adipose tissue at 200× magnification.
Figure 3A:
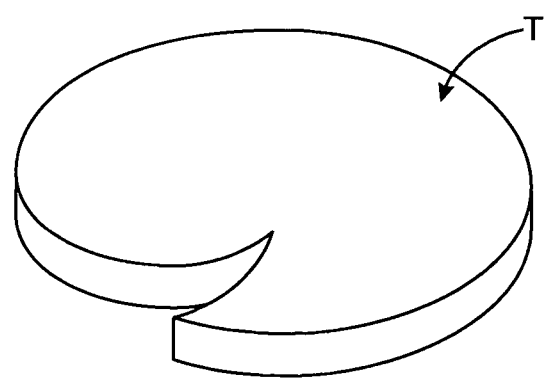
FIG. 3a is a schematic illustration of a vortex ultrasound transducer/applicator design in accordance with the present invention.

The present invention implements an applicator design that incorporates the phase shifts mechanically, not electronically. This is mathematically equivalent to letting N→∞, that is letting the number of sectors become infinite, or making a continuously curving shape, as shown in FIG. 3a, that yields a 2πm phase shift after one revolution. The applicator would also be preset with spherical focus. As one can see, this shape would be difficult to machine in a solid piezoelectric ceramic material. But one can easily imagine molding a piezocomposite into this shape using steel molds manufactured with a ball end mill or EDM (electric discharge machining) machine. FIG. 3a also illustrates the generic shape of a continuously variable sector-vortex applicator made by splitting a spherical bowl transducer T along a radius and translating one split edge axially in relationship to the other edge.

Figure 3B:
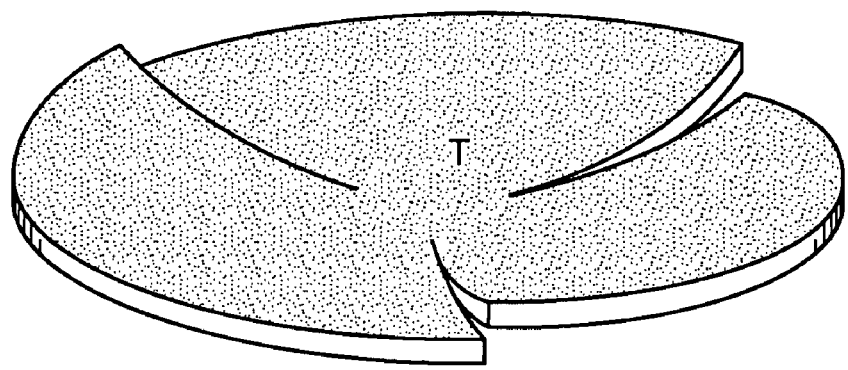
FIGS. 3b and 3c illustrate the transducer having a 2 πm phase shift where multiple variable values of m are formed.
Figure 3C:
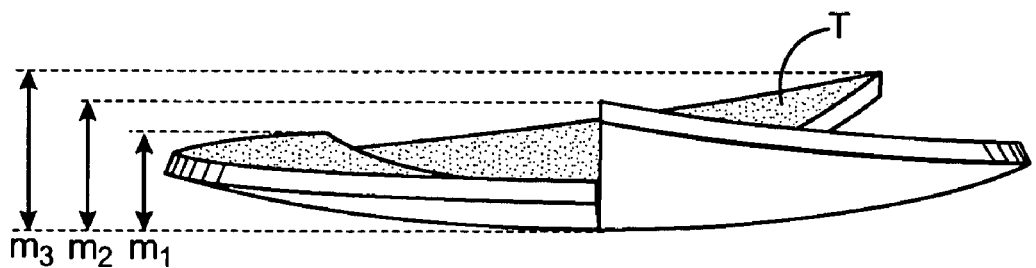
Figure 4A:
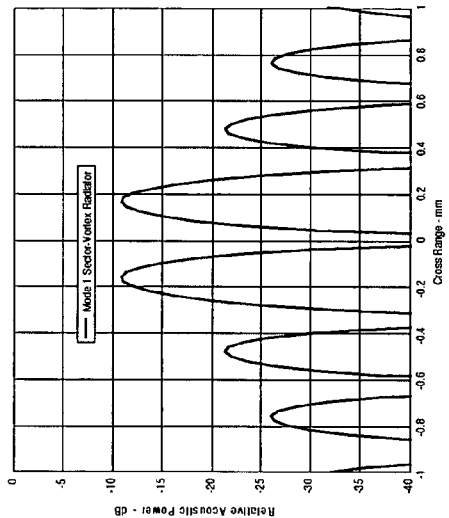
FIGS. 4a-4d show a cross-sectional focal zone intensity distributions for a series of sector-vortex applicators, modes 0 through 3, demonstrating the annular structure of the field patterns and the widening of the annulus as a function of mode number.
Figure 4B:
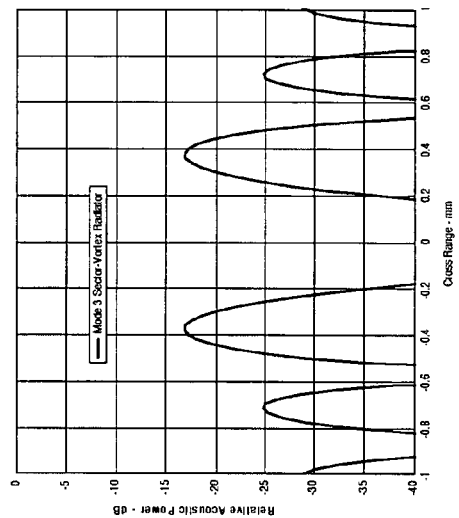
Figure 4C:
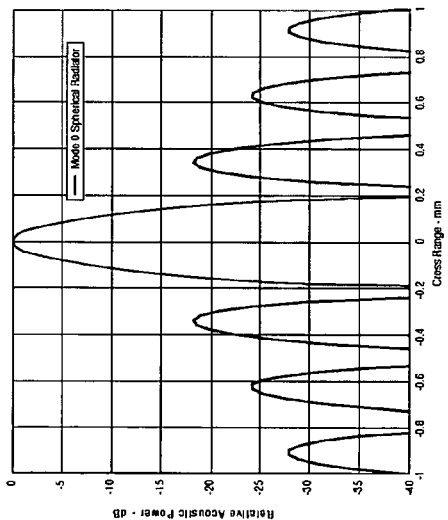
Figure 4D:
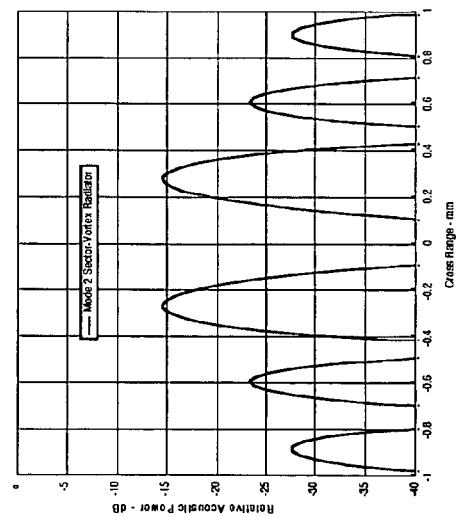

Alternatively, the transducer face may have two or more offsets in the edge. In FIGS. 3b and 3c there is a transducer T illustrated as having three axial offsets along the transducer edge, and each offset has a different value m ($m_1$, $m_2$, $m_3$). While three offsets are illustrated, the number of offsets, shape and size of the offsets may be adapted to produce a non-ideal focal region of any shape and intensity within the limit of the transducer's total capacity.

A $2\pi$ phase shift (mode number=1) corresponds to one wavelength of the driving frequency; at 4 MHz in water, this is 380 μm. Thus, for mode 1, the discontinuity at the split on the edge of the spherical bowl would then be 380 μm, mode 2 (being 2 πm as described in the parent application), 760 μm, and so on. The mode number may be a non-integral, or non whole number to produce additional variations. For example, if the mode number is 1.5, the value of the 4 MHz transducer will be 570 μm. Splitting a spherical bowl made of piezocomposite along one radial line, and forming it with a discontinuity on the order of 1 mm is possible.

FIGS. 4a-4d show the cross-sectional focal patterns for modes 0, 1, 2, and 3, respectively. Mode 0 reduces just to the simple spherical radiator, and serves as the standard by which to judge the increase in focal zone area in other designs.

Theoretically, the field along the central axis of the sector-vortex applicator is zero and would not contribute to tissue lysis. However, heat generated in the annulus will flow into this region and will not have ready access to a heat sink. It is expected, if the annulus is not too large, that the temperature will rise to therapeutic levels under interesting drive conditions, forming a large solid lesion.

Figure 5A:
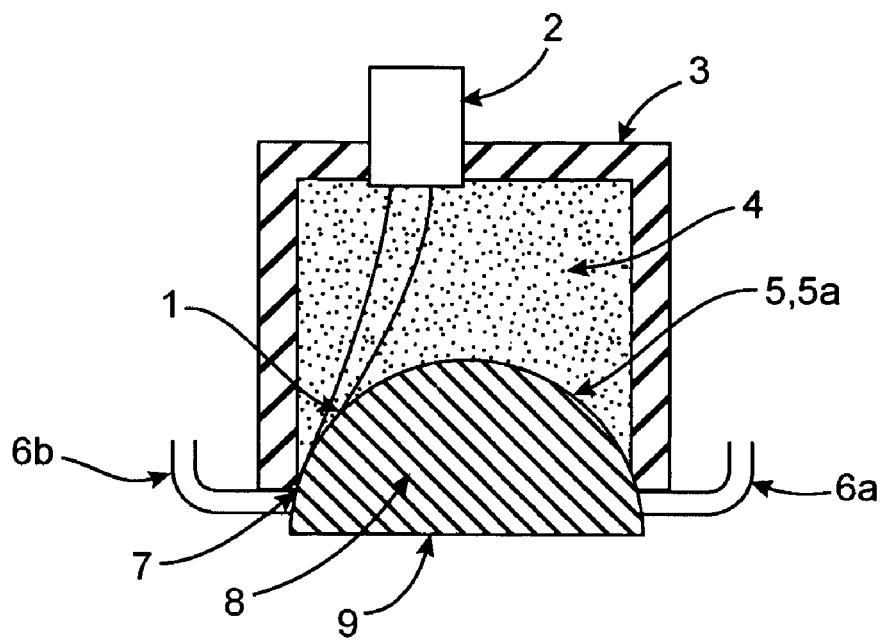
FIGS. 5a and 5b is a further illustration of an embodiment of the present invention.
Figure 5B:
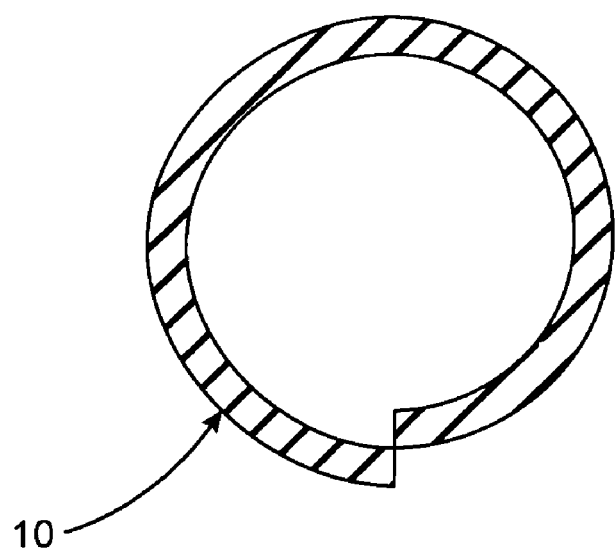

Based on the proceeding description, it is possible to produce a vortex transducer. The present invention comprises a mechanically formed vortex ultrasound transducer capable of producing at least one, substantially annular focal region(s) when said transducer is excited. The transducer may incorporate a solid piezoelectric material or a composite piezoelectric material. Furthermore the transducer may incorporate one or more matching layers. The transducer may incorporate a filler material in front of the transducer or backing material in back of the transducer. The transducer may also be formed from a single contiguous piezoelectric element. See FIGS. 5a and 5b, where the reference numbers are as follows:

1. Back electrode connection and wire
2. Electrical connector
3. Transducer housing
4. Backing material
5. Piezoelectric element
5a. Matching layer(s) on front of piezoelectric element
6a.-6b. Fluid inlet and outlet for cooling
7. Front electrode connection and wire
8. Filler material
9. Face material
10. Piezoelectric material A method of making the transducer of the present invention is also provided. The method comprises the steps of: first shaping a piezoelectric ceramic into a desired form, the form having a front end and a back end. Second dicing the front end create a plurality of elements, the elements being attached to the back end and separated by dicing channels. Third filling the dicing channels with a resin material and allowing the resin to gel. Fourth, creating a transducer form by removing the back end such that the elements are separated from one another. Fifth, pressing the transducer form into a mold and heating the transducer form such that the resin is heated above the B-state and allowing the resin to cross link and cool in a set shape. Sixth, treating at least one surface of the transducer form with a conductive material such that all elements are in contact with the conductive material. An additional step involves the formation of one or more shaped irregularities to produce a non-ideal focal zone when the transducer is excited. This step can be inserted into the steps above where ever desired and there is no best order for the introduction of this step. The shaped irregularity can be part of the original forming of the transducer form, or it can be created later by cutting or grinding the transducer form such that the desired irregularity is introduced.

Figure 6A:
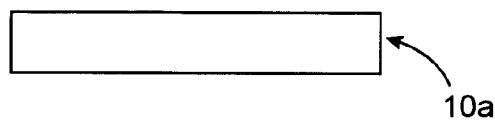
FIGS. 6a-6g illustrate a process for making transducers in accordance with the present invention.
Figure 6E:
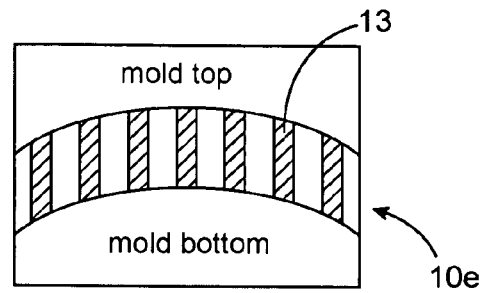
Figure 6B:
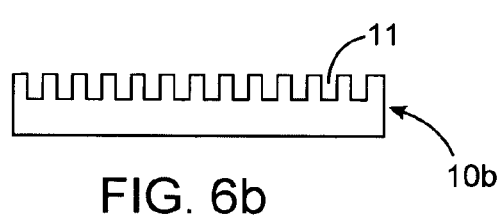
Figure 6C:
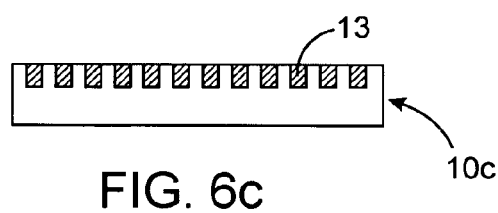
Figure 6F:
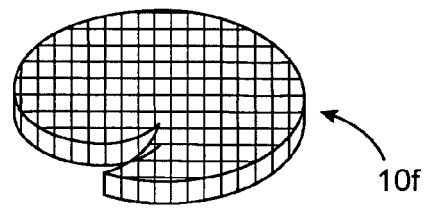
Figure 6D:
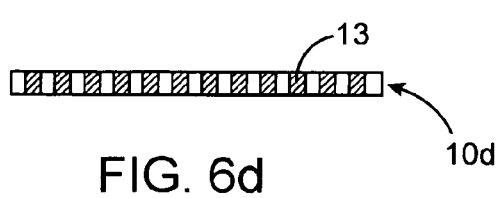

The manner of producing the transducer is detailed below. First, the piezoelectric material is formed into a desired form (FIG. 6a). The form may include the irregularity used to mechanically create the vortex transducer effect, or the irregularity can be introduced into the finished transducer form. The shaping of the piezoelectric ceramic into a desired form follows procedures well established in the art of making ultrasound transducers. The principal embodiment calls for a flat shape having sufficient size to be later molded into the desired three dimensional form. Otherwise there is no restriction or requirement on the formation process. Similarly the dicing of the ceramic is also well known. In the second step the ceramic is diced such that there is sufficient depth in the dicing channels 11 to allow a resin like material to fill the channels (FIG. 6b). The filling of the channels with a polymer (e.g. epoxy or urethane 13) provides a solid material to support and maintain the elements in a fixed position relative to one another (FIG. 6c). Once the polymer 13 is set sufficiently to hold the elements in place without the structural support of the ceramic back plate, the back plate is removed (FIG. 6d). Now the transducer form comprises the individual elements and the polymer used to suspend the elements and hold them in place.

The resulting two-phase composite material can be tailored to have a number of interesting electro-mechanical and purely mechanical properties by the choice of parameters like ceramic volume fraction and polymer filler material. Of particular interest in permanently forming piezocomposites into interesting shapes is the use of hardset (high durometer) thermoset resin systems such as epoxy as the polymer filler. The set epoxy in the composite can be partially cured at a relatively low temperature where it "gels," or turns substantially solid from a liquid state. At a slightly higher temperature, the epoxy can then progress into a B-stage partially cross-linked cure which is quite hard, but very brittle. At this level the piezocomposite can be processed easily by grinding to a thickness as a flat plate and applying electrodes. As a final step, the piezocomposite can then be reheated slightly past the B-stage temperature where it softens considerably and can be formed into shapes. Commonly, the piezocomposite is placed in a warm bottom half of a mold that allows the plate to take the shape of the mold, a top half of the mold is then clamped to the bottom half, and then the mold is heated to a high final curing temperature. At this point, the epoxy filler cures to a fully cross-linked, tempered, stage over a period of time determined by the resin system. The resulting molded piezocomposite now has a shape that takes on the shape of a lens. In this manner, a piezoelectrically active lens can be made that is quite rugged, eliminating the need for separate focusing lenses.

Figure 6G:
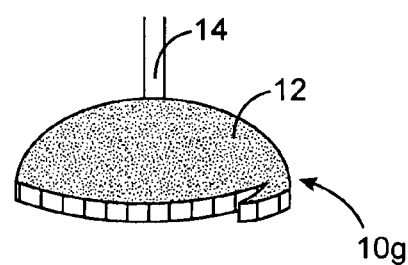

The next step provides an essential process step of the present invention. That is the molding of the transducer form to shape the elements and polymer (epoxy) combination into a shaped transducer (FIG. 6e). The form selected will dictate the focal range, depth and shape of the ultrasound focal zone. Thus the mold must be carefully determined and created since it is not possible to electronically steer the transducer when it is completed. When the transducer form is in the mold, the mold and transducer form are heated until the resin/epoxy is heated past the B-stage of the filler material. This makes the epoxy/resin softer so the transducer form can be properly shaped. The final shaped transducer (FIG. 6f) is then coated with a conductive material and electronically connected (FIG. 6g) to an activation device such as a high voltage supply (not shown).

The reference numbers used in FIGS. 6a-6g are as follows:
10a Piezoelectric ceramic
10b Dized ceramic
10c Filled with epoxy 13
10d Back removed
10e Heat molding
10f planar transducer with irregularity
10g Heat molded with irregularity and conductive layer 12 and electrical connection 14

The transducer can be made to operate either narrowband (roughly at one frequency) or broadband (over a range of frequencies). The decision on narrow or broadband will be left to the designer to choose based on the specific application. The designer should consider the beam pattern the vortex transducer will produce before finalizing the design. The beam shape will produce a double funnel focus field similar to that described in the prior art; however, with the simplified transducer of the present invention, there will be no need for complex electronics to steer or focus the beam, or run a complex pattern of individual element activations.

Additional modifications and variations of the present invention are possible in light of the above teachings and the description provided herein is not to be meant as limiting the invention to the descriptions provided. It is understood those skilled in the art will be able to utilize the present teaching without substantial variation, and such practices are within the intended scope of the present invention and the appended claims.

What is claimed is:

1. A medical ultrasound transducer comprising a piezoelectric transducer body having a front surface, a back surface, a peripheral edge between said front surface and said back surface, and an axis, wherein the front surface and back surface are each transverse to the axis, and wherein the piezoelectric transducer body has a spherical bowl geometry and is split along a radius thereof so that the peripheral edge is divided into adjacent portions which are axially offset from each other in a pattern which produces at least one substantially annular 2 πm phase shift focal region(s) when said transducer is excited, where m is a non-whole number value other than zero.

2. The transducer of claim 1, further comprising a filler material over the front surface of the transducer.

3. The transducer of claim 1, wherein the piezoelectric transducer body comprises a single contiguous piezoelectric element.

4. The transducer of claim 1, further comprising a backing material over the back surface of the transducer.

5. The transducer of claim 1, wherein the spherical bowl piezoelectric transducer body has more than one split along a radius thereof.

6. A medical ultrasound transducer having a front surface, a back surface, a peripheral edge between said front surface and said back surface, and an axis, wherein the front surface and back surface are each transverse to the axis, and wherein the transducer comprises a piezoelectric body having a spherical bowl geometry which is split along a radius thereof so that the peripheral edge is divided into adjacent portions which are axially offset from each other in a pattern which produces a 2 πm phase shift focal region for each offset when said transducer is excited, where m is any real number other than zero.

7. The transducer of claim 6, wherein the front surface and the back surface of each adjacent portion of the peripheral edges have the same axial offset value.

8. The transducer of claim 6, wherein the front surface and the back surface of each adjacent portion of the peripheral edges have different axial offset values.

* * * * *